(12) United States Patent
Seckin

(10) Patent No.: US 10,493,171 B2
(45) Date of Patent: Dec. 3, 2019

(54) LAPAROSCOPIC SURGERY SOLUTION AND METHOD OF USING THE SAME

(71) Applicant: Tamer Ahmet Seckin, New York, NY (US)

(72) Inventor: Tamer Ahmet Seckin, New York, NY (US)

( * ) Notice: Subject to any disclaimer, the term of this patent is extended or adjusted under 35 U.S.C. 154(b) by 482 days.

(21) Appl. No.: 14/991,982

(22) Filed: Jan. 10, 2016

(65) Prior Publication Data

US 2016/0199514 A1   Jul. 14, 2016

(51) Int. Cl.
*A61K 49/00* (2006.01)
*A61B 1/313* (2006.01)

(52) U.S. Cl.
CPC .......... *A61K 49/006* (2013.01); *A61B 1/3132* (2013.01)

(58) Field of Classification Search
None
See application file for complete search history.

(56) References Cited

U.S. PATENT DOCUMENTS 6,696,430 B1 * 2/2004 Melles ................. A61K 49/006
424/9.6

FOREIGN PATENT DOCUMENTS

JP         01294633 A  * 11/1989

OTHER PUBLICATIONS

Lessey et al. Intraoperative detection of subtle endometriosis: a novel paradigm for detection and treatment of pelvic pain associated with the loss of peritoneal integrity. 2012 J. Vis. Exp. 70(e4313): 6 p. (Year: 2012).*
White et al. Is Hartmann's the solution? 1997 Anaesthesia 52: 422-427. (Year: 1997).*

* cited by examiner

*Primary Examiner* — Jennifer A. Lamberski
(74) *Attorney, Agent, or Firm* — Preston Smirman; Smirman IP Law, PLLC

(57) ABSTRACT

The present invention provides a laparoscopic surgery method comprising inspection of peritoneal surfaces under an isotonic solution comprising a contrast enhancing agent using near contact scanning by a laparoscope. Accordingly, the method according to the current invention comprises introducing the solution and the contrast enhancing agent into the retroperitoneal space through a catheter or a channel of a laparoscope using an irrigation pump. The present invention provides also an isotonic laparoscopy solution comprising a contrast enhancing agent enhancing the contrast of the laparoscopic view.

10 Claims, 3 Drawing Sheets

LAPAROSCOPIC SURGERY SOLUTION AND METHOD OF USING THE SAME

TECHNICAL FIELD

The present invention relates to a liquid solution for a laparoscopic surgery and a laparoscopic surgery method using such a liquid solution.

BACKGROUND ART

Endometriosis, a disease affecting approximately 10% of the female population, requires laparoscopy and histologic confirmation for diagnosis. Laparoscopic recognition of endometriosis lesions can be extremely challenging even for the experienced surgeon due to the protean appearances of endometriosis. Visual appearance of what is classically described as pigmented, dark lesions are easily spotted while the non-pigmented, more prevalent white lesions, also known as "subtle" lesions, pose difficulty for recognition. This is due to a wide unrestricted light spectrum, light reflection, and gas pressure used in laparoscopic surgery. An endometriosis surgeon should be familiar with all appearances of endometriosis. The classical or typical lesions are quickly visualized with varying colors from red to black, but they are always outnumbered by atypical and microscopic endometriosis, which is not easily recognized. The inexperienced surgeons who do not practice excision technique may miss these occult and deep lesions. A wide variety of angiogenesis and inflammatory process is taking place in the peritoneum and must be recognized in addition to the typical and atypical lesions of endometriosis. Laparoscopy may be performed via the abdominal wall and the peritoneal cavity or via the vagina and the pouch of Douglas. The benefit of this second route of entry for the patients is that the intervention is minimally invasive, with no scar and performed typically under local anaesthesia. This procedure is deemed to be safe because it is carried out entirely below the peritoneum, eliminating the risk of peritonitis if the bowel is inadvertently punctured. In addition the procedure is carried out without disturbing the position of the internal organs, thus allowing the detection of abnormalities normally not seen during conventional laparoscopy.

In gynecology, diagnostic laparoscopy may be used to inspect the outside of the uterus, ovaries and fallopian tubes, for example in the diagnosis of female infertility or endometriosis. Usually, there is one incision near the navel and a second near to the pubic hairline. During laparoscopy, the abdominal cavity is pressurized using a gas, typically carbon dioxide, for providing a better view to the surgeon. US20130131457 A1, which is incorporated here by reference, describes a procedure via the vagina and the pouch of Douglas and an instrument thereof for eliminating the risk of a puncture or injury e.g. to major blood vessels.

US20130131457 A1, which is incorporated here by reference, describes a further instrument for introduction through trans-vaginal route and the use of a liquid for pressurizing the pelvic cavity instead of a gas. Such a liquid may typically be a saline solution such as normal saline (0.90% w/v of NaCl, about 300 mOsm/L or 9.0 g per liter).

There is still a need for enhancing the view of the surgeon during a laparoscopy, especially for inspection for superficial collateral pathology, Leopard Spots; inspection for retroperitoneal fibrosis and inspection for micro endometriosis implants.

DISCLOSURE OF THE CURRENT INVENTION

The present invention provides a laparoscopic surgery method comprising inspection of peritoneal surfaces under a colored solution comprising a contrast enhancing agent, typically using near contact scanning by a laparoscope. Distinct morphological features detected with the technique of the current invention are eventually confirmed as inflammation and endometriosis with pathological samples stained with Hemotoxylin and eosin (HE) and by using immunohistochemical staining of CD-10, for which it is often positive for both, with stromal cells alone more commonly found than glands/stroma. The technique of the current invention easily identifies normal peritoneum and its texture is easily identified. This method assists the surgeon to target the lesion by clear recognition of subtle peritoneal changes in endometriosis. Assisted by enhancing contrast and eliminating the yellow and red spectrums, the surgeon is now more easily able to perform tedious and precisely accurate excision surgery without unnecessary removal of normal peritoneum. This technique not only will improve results for excision surgery, but also opens a future window of understanding and likely will bring a new definition to the aged concepts about endometriosis. Changing the color spectrum and using hydrofloatation with contrastcolor and retroperitoneal distention helps to visualize endometriosis otherwise undetectable by standard laparoscopic inspection. Accordingly, the method according to the current invention comprises introducing the colored solution and the contrast enhancing agent into the abdominal cavity, preferably into the retroperitoneal space, preferably through a catheter or a channel of a laparoscope, preferably using an irrigation pump. Preferably 100 mL to 2 L, more preferably 100 mL or 1 L, of colored solution may be introduced for hydrofloatation in the retroperitoneal space and hydro-distention of peritoneum to create contrast under peritoneal membrane. Accordingly, the method according to the current invention comprises distending the peritoneum and trapping the colored solution comprising the contrast enhancing agent in the fibrillary collagen based aerolar tissue among blood vessels, nerves and organs.

According to the invention, the contrast enhancing agent may be dissolved in the solution before introduction of the solution into the abdominal cavity; alternatively, first, the solution may be introduced into the abdominal cavity and then the contrast enhancing agent be introduced into the abdominal cavity to calibrate the contrast rate in the abdominal space. The amount of the contrast enhancing agent in the solution may be increased stepwise, preferably automatically by an appropriate means for administering the contrast enhancing agent, and the view of the laparoscope may be checked in each step to stop introducing the contrast enhancing agent.

According to the invention, colored solution and the contrast enhancing agent may be transmitted into the abdominal cavity via the abdominal wall and the peritoneal cavity or via the vagina and the pouch of Douglas. Accordingly, the method according to the current invention comprises distending the peritoneum such that the pressure in the abdominal space or in the retroperitoneal space is arranged as less than the venous pressure of the patient, specifically up to 80 mmHg or calibrated according to the venous pressure of the patient.

According to the invention, the contrast enhancing agent may be Methylene Blue (designated as CI 52015; $C_{16}H_{18}N_3SCl$); 3,7-bis(dimethylamino)-phenothiazin-5-ium chloride). The contrast enhancing agent may be alternatively Indigo Carmine or Indocyanine Green. The contrast enhancing agent may be alternatively any combination of Methylene Blue, Indigo Carmine or Indocyanine Green.

The method according to the current invention provides elimination of light reflection, elimination of red and yellow colors in the abdominal cavity due to contrast enhancing agent, and elimination of direct gas pressure on the peritoneal surfaces so that projectile surface vegetative lesions start to hydro float. Further, retroperitoneum hydro-distention and creation of blue color contrast in the background makes it possible to identify peritoneal micro defects to determine excision boundaries and inspection of retroperitoneal space under blue colored solution for micro invasion and fibrosis.

According to the invention, in order to provide the colored solution, 1 to 250 mg, preferably 10 to 50 mg, more preferably 30 mg contrast enhancing agent may be dissolved in 1 L sterile water or preferably in Normal Saline, more preferably in an isotonic solution containing 6.5 g NaCl, 0.42 g KCl, 0.25 g $CaCl_2$ and 0.2 g of sodium bicarbonate dissolved in one litre of distilled water, more preferably containing per 1000 mL:

130 to 131 mEq of sodium ion=130-131 mmol/L
109 to 111 mEq of chloride ion=109-111 mmol/L
28 to 29 mEq of lactate=28-29 mmol/L
4 to 5 mEq of potassium ion=4-5 mmol/L
3 to 4 mEq of calcium ion=1.5-2 mmol/L more preferably containing per 1000 mL:

130 mEq of sodium ion=130 mmol/L
109 mEq of chloride ion=109 mmol/L
28 mEq of lactate=28 mmol/L
4 mEq of potassium ion=4 mmol/L
3 mEq of calcium ion=1.5 mmol/L or:

131 mEq of sodium ion=131 mmol/L
111 mEq of chloride ion=111 mmol/L
29 mEq of lactate=29 mmol/L
5 mEq of potassium ion=5 mmol/L
4 mEq of calcium ion=2 mmol/L.

Each 100 mL of such an isotonic solution may contain: Sodium chloride 600 mg; sodium lactate, anhydrous 310 mg; potassium chloride 30 mg; calcium chloride, dihydrate 20 mg. Such an isotonic solution may further contain sodium hydroxide and may further contain hydrochloric acid for pH adjustment. Heparin may be added to such a solution (5 IU per L).

Calcium Chloride, USP is chemically designated calcium chloride, dihydrate ($CaCl_2 \cdot 2H_2O$), white fragments or granules freely soluble in water. Potassium Chloride, USP is chemically designated KCl, a white granular powder freely soluble in water. Sodium Chloride, USP is chemically designated NaCl, a white crystalline powder freely soluble in water. Sodium Lactate, USP is chemically designated $NaC_3H_5O_3$, a 60% aqueous solution miscible in water.

During electro-surgical procedures, instead of an electrolyte solution, % 1.5 Glycine (NH2CH2COOH) solution 1.5 g glycine per 100 mL water solution may be used in a method according to the invention. Alternatively, a 5% Mannitol solution (5 g Mannitol per 100 mL) or a solution containing Sorbitol 2.70 g and Mannitol 0.54 g in 100 mL sterile water. Mannitol, USP is chemically designated D-mannitol (C6H14O6), white crystalline powder or free-flowing granules, freely soluble in water. Sorbitol, NF is chemically designated D-glucitol (C6H14O6), white powder, granules or flakes very soluble in water.

Alternatively, 4% icodextrin solution may be used as a solution during the method according to the invention.

Hence, using a colored laparoscopy solution during a laparoscopy, current invention provides contrast in the abdominal cavity while keeping the peritoneum distended due to applied pressure.

These and other objects of the present invention will be apparent from the drawings, claims and detailed descriptions herein.

BRIEF DESCRIPTION OF THE DRAWINGS

The accompanying drawings, referred to herein and constituting a part hereof, illustrate preferred embodiments of the present invention and together with the description, serve to explain the principles of the present invention, wherein.

DESCRIPTION OF THE EMBODIMENTS

Figure 1:
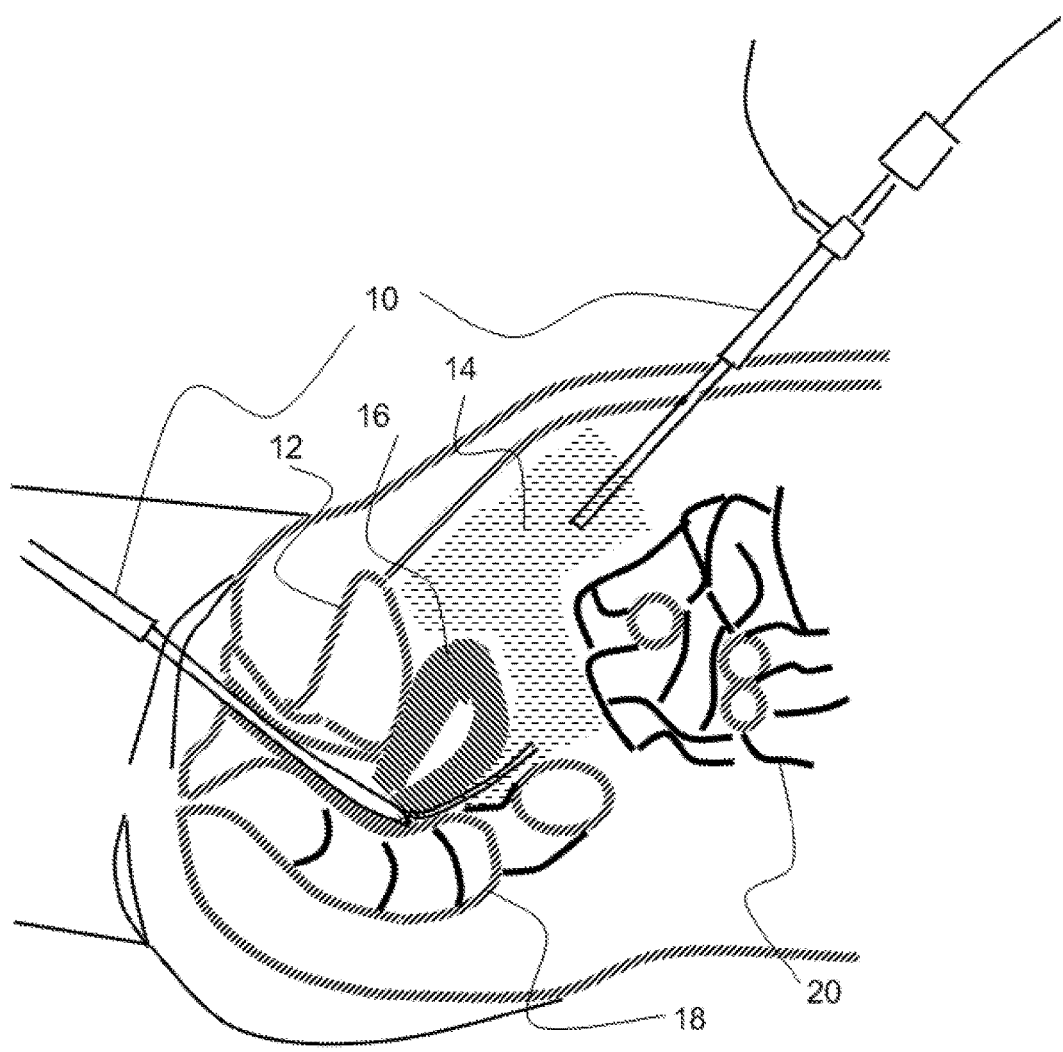
FIG. 1 is a partial cross-sectional side view of a female body comprising an embodiment of the present invention.

Referring to FIG. 1, there is illustrated in cross-sectional view of a partial female body showing the abdominal cavity (14), laparoscopes (10) placed through the abdominal wall and the transvaginal-transdouglas route, the uterus (16), the bladder (12), the rectum (18) and the small intestine (20).

According to the embodiment shown in FIG. 1, the abdominal cavity (14) is filled with 1 L of a solution containing sodium chloride 6000 mg; sodium lactate, anhydrous 3100 mg; potassium chloride 300 mg; calcium chloride, dihydrate 200 mg, further comprising 30 mg Methylene Blue. However other solutions and other contrast enhancing agents may be used as described above. The blue colored solution distends the peritoneum, makes the tissues in the retroperitoneum hydrofloat and provides contrast in the background of the distended peritoneum and in the retroperitoneum during near contact scanning with the laparoscope (10). The amount of the Methylene Blue in the solution may be increased stepwise, e.g. with 10 mg increments per L of the solution beginning with 10 mg/L, and the view of the laparoscope may be checked in each step to stop introducing the contrast enhancing agent. This may be performed automatically by an appropriate means for administering the contrast enhancing agent. Any other appropriate increments may be chosen for obtaining the best contrast calibration.

Figure 2:
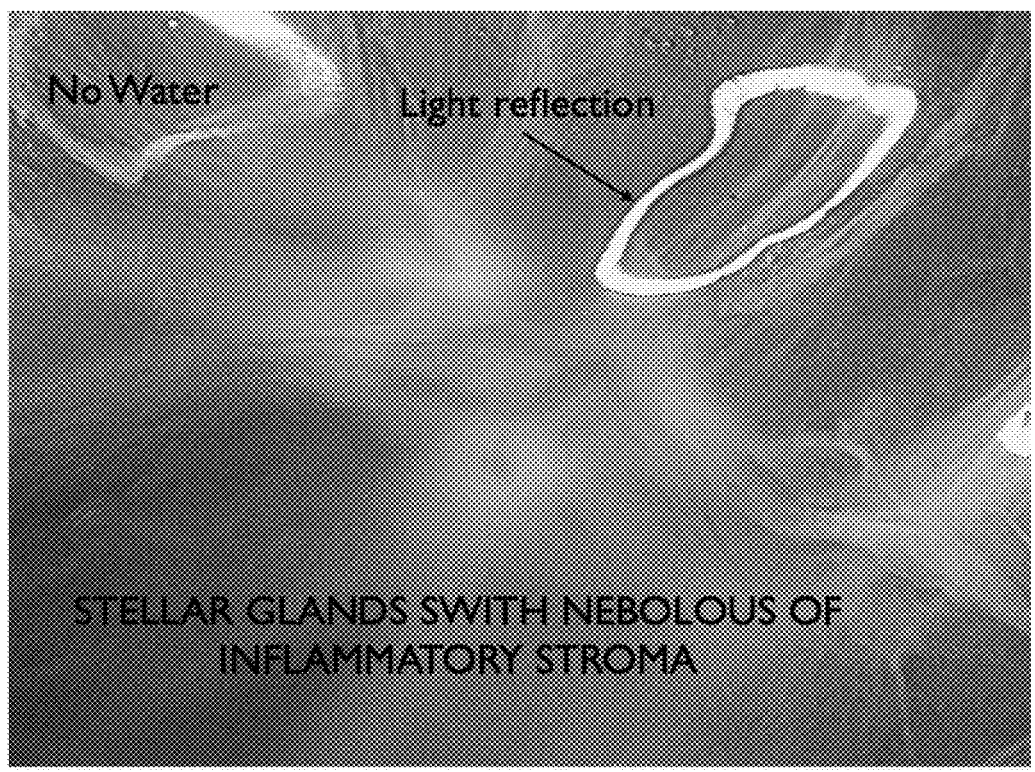
FIG. 2 is a view of peritoneum without using a colored solution according to the invention.
Figure 3:
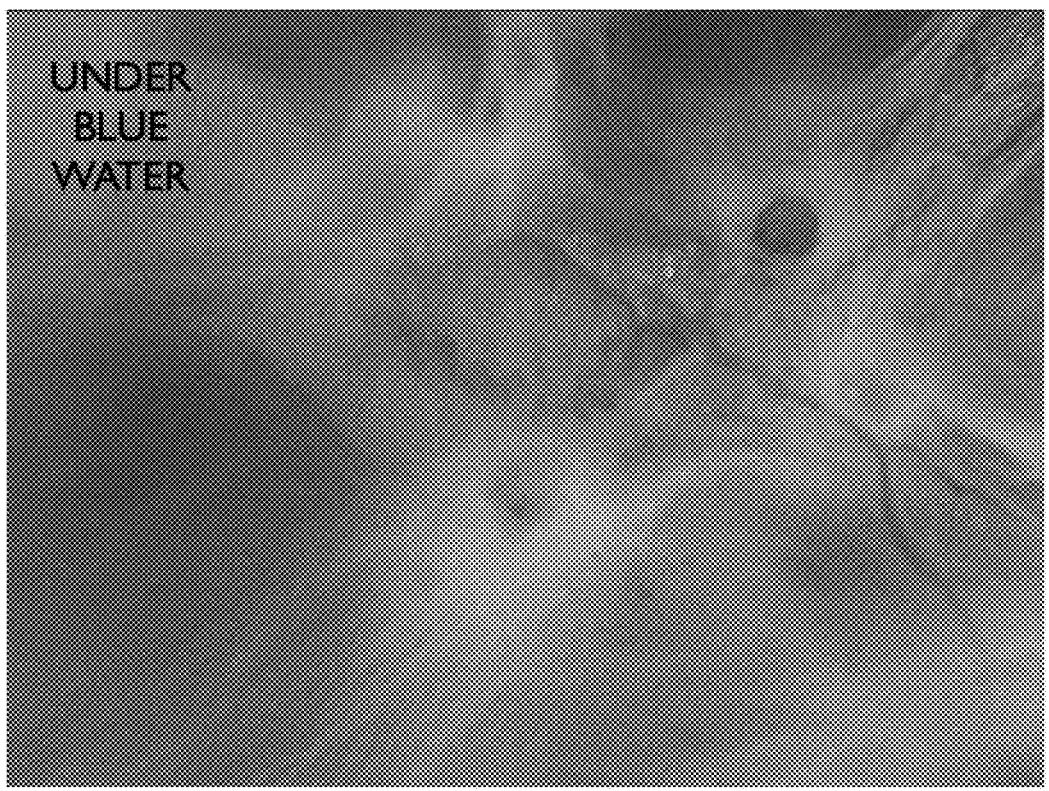
FIG. 3 is a view of peritoneum under a colored solution according to the invention.

FIG. 2 is a view of peritoneum through a laparoscope without using a colored solution, therefore light from the laparoscope is reflected and the picture has limited contrast. On the other hand, FIG. 3 shows a view of peritoneum through a laparoscope (10) under a blue colored solution according to the embodiment shown in FIG. 1, hence the picture has more contrast such that the tissues and blood vessels in the background and in the peritoneum are visible.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

The invention claimed is:

1. A laparoscopic surgery method comprising:
   introducing a laparoscope into an abdominal cavity;

introducing a liquid solution into a retroperitoneal space, wherein said retroperitoneal space gets filled with at least about 100 mL of said liquid solution for hydro-floatation and hydro-distention;

introducing a contrast enhancing agent into the abdominal cavity for calibrating the contrast of the view of said laparoscope;

dissolving said contrast enhancing agent in said liquid solution;

trapping said liquid solution comprising said contrast enhancing agent in said retroperitoneal space;

scanning the peritoneum and/or the tissues in said retroperitoneal space under said liquid solution comprising said contrast enhancing agent using said laparoscope.

2. A laparoscopic surgery method according to claim 1, wherein introducing said laparoscope into said abdominal cavity comprises introducing said laparoscope via the abdominal wall and the peritoneal cavity or via the vagina and the pouch of Douglas.

3. A laparoscopic surgery method according to claim 1, wherein introducing said liquid solution into said retroperitoneal space comprises introducing said liquid solution and said contrast enhancing agent via the abdominal wall and the peritoneal cavity or via the vagina and the pouch of Douglas.

4. A laparoscopic surgery method according to claim 1, further comprising filling the retroperitoneum with 100 mL to 2 L of said liquid solution.

5. A laparoscopic surgery method according to claim 1, wherein said contrast enhancing agent is dissolved in said liquid solution before said liquid solution is introduced into the retroperitoneal space.

6. A laparoscopic surgery method according to claim 1, wherein said liquid solution is introduced into the retroperitoneal space first, and then said contrast enhancing agent is introduced into the abdominal cavity.

7. A laparoscopic surgery method according to claim 1, further comprising increasing the amount of said contrast enhancing agent in said liquid solution stepwise, and checking the view of the laparoscope in each step to stop mixing said contrast enhancing agent to said liquid solution.

8. A laparoscopic surgery method according to claim 1, wherein said contrast enhancing agent is one of Methylene Blue, Indigo Carmine or Indocyanine Green, or a mixture of at least two thereof.

9. A laparoscopic surgery method according to claim 1, further comprising dissolving 1 to 250 mg of said contrast enhancing agent into one of the following:
1 L sterile water;
Normal Saline;
an isotonic solution containing 6.5 g NaCl, 0.42 g KCl, 0.25 g $CaCl_2$ and 0.2 g of sodium bicarbonate in one litre of distilled water;
an isotonic solution containing per 1000 mL:
  130 to 131 mmol/L sodium ion,
  109 to 111 mmol/L chloride ion,
  28 to 29 mmol/L lactate,
  4 to 5 mmol/L potassium ion, and
  1.5 to 2 mmol/L calcium ion;
an isotonic solution containing per 1000 mL:
  130 mmol/L sodium ion,
  109 mmol/L chloride ion,
  28 mmol/L lactate,
  4 mmol/L potassium ion, and
  1.5 mmol/L calcium ion; and
an isotonic solution containing per 1000 mL:
  131 mmol/L of sodium ion,
  111 mmol/L chloride ion,
  29 mmol/L lactate,
  5 mmol/L potassium ion, and
  2 mmol/L calcium ion.

10. A laparoscopic surgery method according to claim 1, wherein said solution is:
a 1.5% Glycine solution;
a 5% Mannitol solution;
a solution containing Sorbitol 2.70 g and Mannitol 0.54 g per 100 mL sterile water; or
a 4% icodextrin solution.

* * * * *